United States Patent [19]

Matsuoka et al.

[11] 4,443,615
[45] Apr. 17, 1984

[54] PROCESS FOR PREPARING INDOLES

[75] Inventors: Manabu Matsuoka, Toyonaka; Michihiro Tsuchiya, Suita; Yoshikazu Tokuda, Toyonaka, all of Japan

[73] Assignee: Tanabe Seiyaku Co., Ltd., Osaka, Japan

[21] Appl. No.: 325,436
[22] PCT Filed: Jun. 25, 1980
[86] PCT No.: PCT/JP80/00146
§ 371 Date: Nov. 10, 1981
§ 102(e) Date: Nov. 10, 1981
[87] PCT Pub. No.: WO82/00032
PCT Pub. Date: Jan. 7, 1982

[51] Int. Cl.³ .......................................... C07D 209/08
[52] U.S. Cl. .................................... 548/489; 548/508
[58] Field of Search ................... 260/319.1; 548/508, 548/489

[56] References Cited

U.S. PATENT DOCUMENTS

| 2,432,586 | 1/1946 | Quarles | 525/159 |
| 2,891,965 | 6/1959 | Voltz et al. | 260/319.1 |
| 3,894,042 | 7/1975 | Tanaka et al. | 260/319.1 |
| 3,991,074 | 11/1976 | Grigoleit et al. | 260/319.1 |
| 4,060,626 | 11/1977 | Hrstka et al. | 424/274 |

FOREIGN PATENT DOCUMENTS

| 49-26626 | 10/1974 | Japan | 260/319.1 |
| 51-95063 | 8/1976 | Japan | 548/508 |
| 53-31660 | 3/1978 | Japan | 260/319.1 |
| 3095965 | 8/1978 | Japan | 548/489 |
| 5108850 | 8/1980 | Japan | 260/319.1 |
| 6055366 | 5/1981 | Japan | 260/319.1 |
| 1385396 | 2/1975 | United Kingdom | 260/319.1 |

OTHER PUBLICATIONS

Barton and Ollis; Comprehensive Organic Chemistry, vol. IV, Pergamon, New York, (1979), p. 461.
Houlihan, Wm., "Indoles, Part I", Heterocyclic Compounds, Wiley-Interscience, New York, (1972), pp. 336, 360, 362.
Gabel, G. O., "Die Wechselwirkung zwishen Athylenolid und Anilin", Berichte 58B, (1925), pp. 577-579.
Knorr, Ludwig, "Ueder den Anidoathylalkohol . . . ", Berichte 30, (1897), p. 909.
McKay and Brownell, "Synthesis . . . Dichlorodiethylamines", J. Org. Chem. 15, (1950), p. 648.
Parera, et al., "Acidic Catalysts for Methylation", Ind. Eng. Chem. Prod. Research Develop. 7, (1968), pp. 259-262.
Yurèv, et al., "Prep. of Monoethanolarylamines", Chem. Abst. 46: 932d.
Burton, et al., Comprehensive Organic Chemistry, vol. 1, p. 594, (1979).
Noller, Carl, Textbook of Organic Chemistry, p. 145, (1966).

Primary Examiner—Donald G. Daus
Assistant Examiner—G. Hendricks
Attorney, Agent, or Firm—Jordan B. Bierman; Linda Bierman

[57] ABSTRACT

An indole of the formula

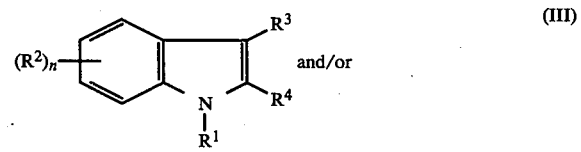

and/or

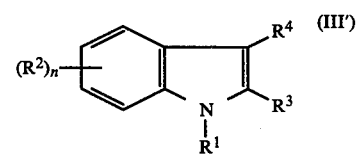

can be prepared by subjecting an aniline of the formula:

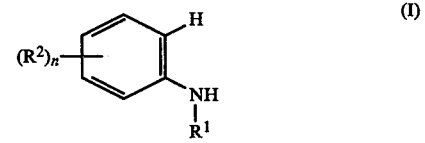

and a glycol or an oxide of the formula:

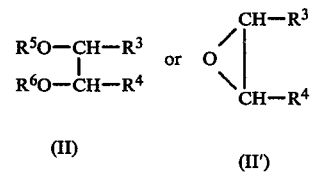

to vapor phase reaction at 250° to 400° C. in the presence of a solid acid catalyst having dehydrating and dehydrogenating activities.

(In the above-mentioned formulae, $R^1$ stands for hydrogen, alkyl, aryl or aralkyl, $R^2$ stands for alkyl or alkoxy, $R^3$ and $R^4$ are the same or different and stands for hydrogen or alkyl, $R^5$ and $R^6$ are the same or different and stand for hydrogen or alkyl, and n is an integer of 0 to 4.)

8 Claims, No Drawings

PROCESS FOR PREPARING INDOLES

TECHNICAL FIELD

This invention relates to a process for preparing indoles. More particularly, it relates to a process for preparing indoles by a vapor phase reaction of anilines with glycols or oxides in the presence of a solid acid catalyst having dehydrating and dehydrogenating activities.

TECHNICAL BACKGROUND

Indoles are useful as starting materials for tryptophan, aromatics, medicines, agricaltural chemicals, stabilizers for polymers, and the like. Various methods have been known for preparation of indoles by a vapor phase reaction. For example, Japanese Patent Publication (unexamined) No. 78163/1973 discloses that indoles are prepared by contacting 2-alkylanilines at 500° to 750° C. with an iron oxide catalyst containing an alkali metal compound. Japanese Patent Publication (unexamined) No. 57966/1973 discloses that indoles are prepared by contacting o-nitroalkylbenzene at 300° to 550° C. with a catalyst containing ruthenium, palladium or platinum. Further, Japanese Patent Publication (unexamined) No. 65266/1977 discloses that indoles are prepared by contacting phenylhydrozines and a carbonyl compound at 300° C. with a Lewis acid (e.g., zinic chloride). Furthermore, Chemical Abstracts, Vol. 62 (1965), 16174h discloses that indole are prepared by contacting aniline and ethanol with an alumina catalyst or an iron oxide-alumina catalyst. Additionally, Chemical Abstracts, Vol. 63 (1965), 11477 g discloses that indole are prepared by contacting aniline and acetylene at 620° to 700° C. with an iron oxide-alumina catalyst. However, the methods described in Japanese Patent Publication (unexamined) No. 78163/1973 and Chemical Abstracts, Vol. 63 (1965), 11477 g are disadvantageous in that the vapor phase reaction must be carried out at a temperature higher than 500° C. In the method described in Japanese Patent Publication (unexamined) No. 57966/1973 it is necessary to use an expensive noble metal catalyst, and the methods described in Japanese Patent Publication (unexamined) Nos. 57966/1973 and 65266/1977 require the use of expensive o-nitro-alkylbenzene or phenylhydrazines as the starting material. Further, the methods described in Japanese Patent Publication (unexamined) Nos. 78163/1973 and 57966/1973, Chemical Abstracts, Vol. 62 (1965), 16174h an ibid. Vol. 63 (1965), 11477 g are disadvantageous in that N-substituted indoles can not be prepared directly.

OBJECTS OF THE INVENTION

An object of the present invention is to provide a method for preparing various indoles including N-substituted indoles from anilines and glycols (or oxides) both of which are less expensive and readily available in the market. Another object of the invention is to provide a method for preparing indoles by carrying out a vapor phase reaction at such a relatively low temperature as 250° to 400° C. Other object of the invention is to provide a method for preparing indoles advantageously in an industrial scale by using a conventional solid acid catalyst instead of such an expensive catlyst as the noble metal catalyst. These and further objects of the invention will become apparent from the following description.

DISCLOSURE OF THE INVENTION

As a result of various inventigations, we have now found that indoles can be readily prepared by reacting anilines with glycols or oxides in the vapor phase in the presence of a solid acid catalyst having dehydrating and dehydrogenating activities. Namely, according to the present invention, an indole of the formula:

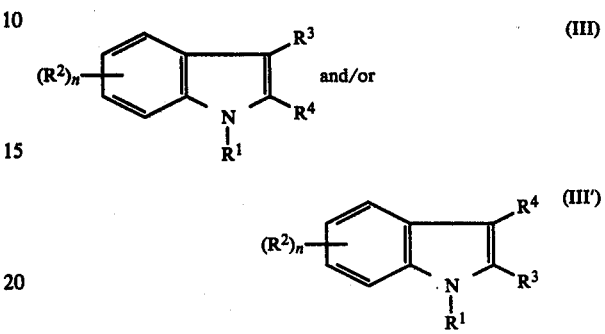

wherein $R^1$ stands for hydrogen, alkyl, aryl or aralkyl, $R^2$ stands for alkyl or alkoxy, $R^3$ and $R^4$ are the same or different and stand for hydrogen or alkyl, and n stands for an integer of 0 to 4, can be prepared by reacting an aniline of the formula:

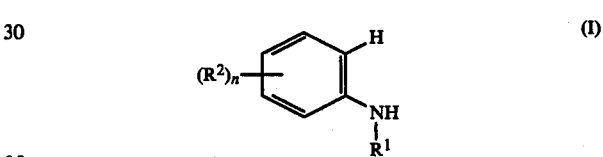

wherein $R^1$, $R^2$ and n are the same as defined above, with either a glycol of the formula:

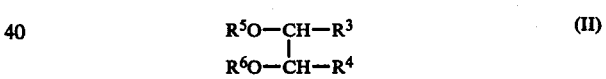

wherein $R^3$ and $R^4$ are the same as defined above, and $R^5$ and $R^6$ are the same or different and stand for hydrogen or alkyl, or an oxide of the formula:

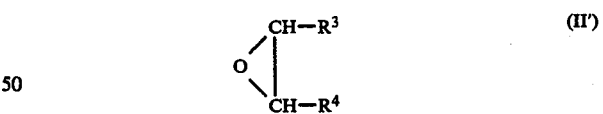

wherein $R^3$ and $R^4$ are the same as defined above, at a temperature of 250° to 400° C. in the vapor phase in the presence of a solid acid catalyst having dehydrating and dehydrogenating activities.

Preferred examples of the aniline to be used in the method of the present invention include those of the formula (I) in which $R^1$ is hydrogen; $C_{1-4}$ alkyl such as methyl, ethyl, n-propyl, isopropyl or n-butyl; aryl such as phenyl or substituted phenyl (e.g., phenyl substituted with $C_{1-4}$ alkyl or $C_{1-4}$ alkoxy such as methylphenyl or methoxyphenyl); or aralkyl such as benzyl or substituted benzyl (e.g., benzyl substituted with $C_{1-4}$ alkyl or $C_{1-4}$ alkoxy such as methylbenzyl or methoxybenzyl), $R^2$ is $C_{1-4}$ alkyl such as methyl, ethyl, n-propyl, isopropyl or n-butyl; or $C_{1-4}$ alkyoxy such as methoxy, ethoxy, n-propoxy or n-butoxy, and n is an integer of 0 to 4.

Representative examples of such aniline include aniline, N-alkylaniline (e.g., N-methylaniline, N-ethylaniline), N-phenylaniline, N-benzylaniline, toluidine (e.g., o-toluidine, m-toluidine, p-toluidine), N-alkyltoluidine (e.g., N-methyl-o-toluidine, N-ethyl-o-toluidine, N-methyl-m-toluidine, N-ethyl-m-toluidine, N-methyl-p-toluidine, N-ethyl-p-toluidine), N-phenyltoluidine (e.g., N-phenyl-o-toluidine, N-phenyl-m-toluidine, N-phenyl-p-toluidine), N-benzyltoluidine (e.g., N-benzyl-o-toluidine, N-benzyl-m-toluidine, N-benzyl-p-toluidine), anisidine (e.g., o-anisidine, m-anisidine, p-anisidine), N-alkylanisidine (e.g., N-methyl-p-anisidine, N-ethyl-p-anisidine), N-phenylanisidine (e.g., N-phenyl-p-anisidine) and N-benzylanisidine (e.g., N-benzyl-p-anisidine).

On the other hand, preferred examples of the glycol include those of the formula (II) in which $R^3$ and $R^4$ are the same or different and are hydrogen or $C_{1-4}$ alkyl such as methyl, ethyl, n-propyl or n-butyl, and $R^5$ and $R^6$ are the same or different and are hydrogen or $C_{1-4}$ alkyl such as methyl, ethyl, n-propyl or n-butyl. Representative examples of such glycol include ethylene glycol, propylene glycol, 1,2-butylene glycol, 2,3-butylene glycol, ethylene glycol monoethyl ether and ethylene glycol mono-n-butyl ether.

Further, preferred examples of the oxide include those of the formula (II') in which $R^3$ and $R^4$ are the same or different and are hydrogen or $C_{1-4}$alkyl such as methyl, ethyl, n-propyl or n-butyl. Representative examples of such oxide include ethylene oxide, 1,2-butylene oxide and 2,3-butylene oxide.

Any solid acid catalysts which have both dehydrating and dehydrogenating activities can be employed as the catalyst in the method of the present invention. Such catalyst includes, for example, a solid acid catalyst containing as its component at least one member selected from aluminum oxide, silicon dioxide and activated charcoal. Representative examples of such catalyst include silica catalyst, alumina catalyst, silica-alumina catalyst, pumice catalyst and activated charcoal catalyst. These catalysts may optionally contain a metal oxide. Examples of the metal oxide include an alkali metal oxide (e.g., sodium oxide, potassium oxide), an alkaline earth metal oxide (e.g., magnesium oxide, calcium oxide), zinc oxide, antimony oxide, bismuth oxide, vanadium oxide, chromium oxide, molybdenum oxide, thungsten oxide, iron oxide, nickel oxide, cobalt oxide, uranium oxide and thorium oxide. It is preferred that the catalyst contains the metal oxide in an amount not more than 50% by weight. Concomitantly, zeolite, either natural or synthetic, is included within the scope of the catalysts of the present invention because it is a kind of the silica-alumina catalysts.

Among the above-mentioned catalysts, a preferred subgenus includes silica catalyst, alumina catalyst, silica-alumina catalyst and these catalysts containing a metal oxide such as sodium oxide, potassium oxide, zinc oxide, chrominum oxide, iron oxide or nickel oxide.

The reaction of the present invention can be carried out by contacting the aniline (I) and the glycol (II) or the oxide (II') with the above-mentioned catalyst at 250° to 400° C. in the vapor phase.

In carrying out the reaction, it is preferred to vaporize the aniline (I) and the glycol (II) or the oxide (II') in a vaporizor and then introduce the vapor of said compounds into a reactor. In this case, preferred molar ratio of the glycol (II) or the oxide (II') to the aniline (I) is 0.5–10:1. Decomposition of the aniline may increase if said molar ratio is less than 0.5:1. On the other hand, side reactions may increase if the molar ratio is more than 10:1. These starting compounds should preferably be introduced into the reactor together with an inert diluent. Such inert diluent includes, for example, steam (water vapor), nitrogen gas, carbon dioxide gas, gaseous benzene, gaseous toluene or a mixture thereof. When such diluent is used, the initial partial pressure of the aniline (I) should be preferably within the range of 0.01 to 0.1 atm. It is preferred to carry out the reaction at 250° to 400° C., especially at 275° to 350° C. The reaction can be carried out either under reduced pressure, under atmospheric pressure or under increased pressure, but it is generally preferred to carry it out under atmospheric pressure. Further, a contact time (W/F) which is defined by the following formula should preferably be within the range of 10 to 1000 g-cat·hr/mole, especially 20 to 200g-cat.hr/mole $$\text{Contact Time } (W/F) = \frac{\text{Amount } (W\,g) \text{ of catalyst packed}}{\text{Total amount per hour } (F\,\text{mole/hr})}$$
of the starting compounds and the diluent which are fed to the reactor The reaction mixture is cooled and collected as a condensed solution. While the resultant indoles and unreacted starting compounds are contained in the condensed solution, they are separated from each other by such a method as extraction or distillation or by converting them to acid addition salts thereof (e.g., hydrochloride). The starting compounds which remain unreacted can be reused for the reaction of the present invention.

The indoles prepared by the above-mentioned method of the present invention include, for example, indole, 1-methylindole, 1-ethylindole, 1-phenylindole, 1-benzylindole, 3-methylindole, 4-methylindole, 5-methylindole, 6-methylindole, 7-methylindole, 1,2-dimethylindole, 1,3-dimethylindole, 1,4-dimethylindole, 1,5-dimethylindole, 1,6-dimethylindole, 1,7-dimethylindole, 3,4-dimethylindole, 3,5-dimethylindole, 3,6-dimethylindole, 3,7-dimethylindole, 1-ethyl-2-methylindole, 1-ethyl-3-methylindole, 1-ethyl-4-methylindole, 1-ethyl-5-methylindole, 1-ethyl-6-methylindole, 1-ethyl-7-methylindole, 1,3-diethylindole, 1,3,7-trimethylindole, 1,3,4-trimethylindole, 1,3,5-trimethylindole, 1,3,6-trimethylindole, 1,2,5-trimethylindole, 1-ethyl-2,5-dimethylindole, 1-ethyl-3,5-dimethylindole, 1-ethyl-3,6-dimethylindole, 1-ethyl-3,7-dimethylindole, 1-benzyl-3-methylindole, 1-methyl-5-methoxyindole, 1,3-dimethyl-5-methoxyindole, 1-benzyl-5-methoxyindole and the like. Concomitantly, two kinds of indoles may be obtained depending on the starting compounds used. For example, 1,3-dimethylindole and 1,2-dimethylindole are obtained by using N-methylaniline and propylene glycol (or propylene (oxide) as the starting compounds. On the other hand, 4-methylindole and 6-methylindole are obtained by using m-toluidine and ethylene glycol as the starting compounds.

The above-mentioned method of the present invention is advantageous in that (I) indoles can be readily obtained from anilines and glycols (or oxides) which are less expensive and readily available in the market; (2) the vapor phase reaction can be carried out at a relatively low temperature (250° to 400° C.); (3) conventional solid acid catalysts can be used as the catalyst, and therefore it is not necessary to use a catalyst containing an expensive noble metal or a poisonous heavy metal; (4) various indoles can be prepared by suitably selecting the starting compounds; and (5) N-substituted indoles can be prepared in a high yield and in a high selectivity. Therefore, the method of the present invention is excellent for preparation of indoles.

The method of the present invention is explained by means of the following Examples, but these Examples should not be construed to limit the scope of the present invention. Throughout Examples, the analytical values were estimated by gas chromatography, and each product was identified by mass spectrum, nuclear magnetic resonance spectrum and infrared adsorption spectrum. Further, the conversion ratio of anilines, selectivity to indoles and yield of indoles are defined as follows:

$$\text{Conversion (\%) of anilines} = \frac{\text{moles of anilines reacted}}{\text{moles of anilines fed}} \times 100$$

$$\text{Selectivity to indoles} = \frac{\text{moles of indoles produced}}{\text{moles of anilines reacted}} \times 100$$

$$\text{Yield of indoles} = \frac{\text{moles of indoles produced}}{\text{moles anilines fed}} \times 100$$

EXAMPLE 1

20 g of "Neobead P" (manufactured by Mizusawa Chemical Industry Co., Ltd.; Chemical compositions (% by weight), Al$_2$O$_3$: SiO$_2$: Na$_2$O=88:9:3) we packed into a tubular quartz-reactor of 22 mm in diameter and 300 mm in length, and heated in a tubular electric furnace. A mixed gas containing an aniline vapor, ethylene glycol vapor, water vapor, nitrogen gas and/or benzene vapor was introduced into the reactor under the following conditions.

| Contact time (W/F): 49.6 g-cat · hr/mole Initial partial pressure (atm): | |
|---|---|
| Reaction Conditions A | |
| Anilines vapor | 0.0205 |
| Ethylene glycol vapor | 0.0409 |
| Water vapor | 0.778 |
| Nitrogen gas | 0.161 |
| Reaction Conditions B | |
| Anilines vapor | 0.0227 |
| Ethylene glycol vapor | 0.0454 |
| Water vapor | 0.771 |
| Nitrogen gas | 0.161 |
| Reaction Conditions C | |
| Anilines vapor | 0.0205 |
| Ethylene glycol vapor | 0.0409 |
| Water vapor | 0.659 |
| Benzene vapor | 0.119 |
| Nitrogen gas | 0.161 |
| Reaction Conditions D | |
| Anilines vapor | 0.0205 |
| Ethylene glycol vapor | 0.0820 |
| Water vapor | 0.619 |
| Benzene vapor | 0.119 |
| Nitrogen gas | 0.161 |

The effluent gas was cooled by a condenser and collected as a condensed solution. The condensed solution was analyzed by gas chromatography about 3 hours after the reaction was started. The results are shown in the following Table 1.

TABLE 1

| No. | Anilines | Reaction conditions | Reaction temperature (°C.) | Main indoles produced | Conversion of anilines (%) | Selectivity to main indoles produced (%) | Yield of main indoles produced (%) |
|---|---|---|---|---|---|---|---|
| 1 | Aniline | A | 350 | Indole | 54.0 | 23.6 | 12.8 |
| 2 | N—Methyl-aniline | A | 325 | 1-Methylindole | 84.6 | 55.7 | 47.1 |
| 3 | N—Ethyl-aniline | A | 300 | 1-Ethylindole | 58.7 | 71.9 | 42.2 |
| 4 | Diphenyl-amine | C | 300 | 1-Phenylindole | 56.0 | 87.9 | 49.2 |
| 5 | N—Benzyl-aniline | C | 300 | 1-Benzylindole | 82.8 | 49.4 | 40.9 |
| 6 | o-Toluidine | A | 325 | 7-Methylindole | 63.9 | 30.8 | 19.7 |
| 7 | N—Methyl-o-toluidine | A | 325 | 1,7-Dimethyl-indole | 61.2 | 33.5 | 20.5 |
| 8 | N—Ethyl-o-toluidine | B | 325 | 1-Ethyl-7-methylindole | 52.3 | 43.9 | 23.0 |
| 9 | m-Toluidine | A | 350 | 4-Methylindole & 6-Methylindole | 69.6 | 34.2 | 23.8 |
| 10 | N—Methyl-m-toluidine | A | 300 | 1,4-Dimethyl-indole & 1,6-Dimethyl-indole | 59.4 | 93.4 | 55.5 |
| 11 | N—Ethyl-m-toluidine | A | 325 | 1-Ethyl-4-methylindole & 1-Ethyl-6-methylindole | 75.9 | 76.0 | 57.7 |
| 12 | p-Toluidine | C | 325 | 5-Methylindole | 69.0 | 25.7 | 17.7 |
| 13 | N—Methyl-p-toluidine | A | 300 | 1,5-Dimethyl-indole | 74.1 | 76.0 | 56.3 |
| 14 | N—Ethyl-p-toluidine | A | 300 | 1-Ethyl-5-methylindole | 72.7 | 57.9 | 42.1 |
| 15 | N—Methyl-p-anisidine | C | 300 | 1-Methyl-5-methoxyindole | 72.7 | 52.0 | 37.8 |
| 16 | N—Benzyl-p-anisidine | D | 300 | 1-Benzyl-5-methoxyindole | 70.1 | 64.3 | 45.1 |

EXAMPLE 2

The reaction was carried out in the same manner as described in Example 1 except that ethylene oxide was used instead of ethylene glycol. The results are shown in the following Table 2.

Reaction conditions
Contact time (W/F): 49.6 g-cat · hr/mole
Initial partial pressure (atm):

| | |
|---|---|
| Anilines vapor | 0.0205 |
| Ethylene oxide vapor | 0.0409 |
| Water vapor | 0.778 |
| Nitrogen gas | 0.161 |

TABLE 2

| No. | Anilines | Reaction temperature (°C.) | Main indoles produced | Conversion of anilines (%) | Selectivity to main indoles produced (%) | Yield of main indoles produced (%) |
|---|---|---|---|---|---|---|
| 1 | Aniline | 350 | Indole | 51.3 | 26.3 | 13.5 |
| 2 | N—Methyl-aniline | 325 | 1-Methyl-indole | 73.4 | 54.6 | 40.1 |
| 3 | N—Ethyl-aniline | 300 | 1-Ethyl-indole | 47.4 | 58.4 | 27.7 |

EXAMPLE 3

The reaction was carried out in the same manner as described in Example 1 except that propylene glycol was used instead of ethylene glycol. The results are shown in the following Table 3.

Contact time (W/F): 49.6 g-cat · hr/mole
Initial partial pressure (atm):

| Reaction conditions A | |
|---|---|
| Anilines vapor | 0.0205 |
| Propylene glycol | 0.0409 |
| Water vapor | 0.778 |
| Nitrogen gas | 0.161 |
| Reaction conditions B | |
| Anilines vapor | 0.0205 |
| Propylene glycol vapor | 0.0409 |
| Water vapor | 0.659 |
| Benzene vapor | 0.119 |
| Nitrogen gas | 0.161 |

TABLE 3

| No. | Anilines | Reaction conditions | Reaction temperature (°C.) | Main indoles produced | Conversion of anilines (%) | Selectivity to main indoles produced (%) | Yield of main indoles produced (%) |
|---|---|---|---|---|---|---|---|
| 1 | Aniline | A | 300 | 3-Methylindole | 63.4 | 31.9 | 20.2 |
| 2 | N—Methyl-aniline | A | 300 | 1,3-Dimethyl-indole | | 46.1 | 23.2 |
| | | | | 1,2-Dimethyl-indole | 50.3 | 14.5 | 7.3 |
| 3 | N—Ethyl-aniline | A | 300 | 1-Ethyl-3-methylindole | | 45.8 | 21.4 |
| | | | | 1-Ethyl-2-methylindole | 46.7 | 13.7 | 6.4 |
| 4 | N—Benzyl-aniline | B | 300 | 1-Benzyl-3-methylindole | 49.5 | 71.0 | 35.1 |
| 5 | o-Toluidine | A | 300 | 3,7-Dimethyl-indole | 70.9 | 79.0 | 56.0 |
| 6 | N—Methyl-o-toluidine | A | 300 | 1,3,7-Trimethyl-indole | 39.4 | 31.9 | 12.6 |
| 7 | N—Ethyl-o-toluidine | A | 300 | 1-Ethyl-3,7-dimethylindole | 29.1 | 40.6 | 11.8 |
| 8 | m-Toluidine | A | 325 | 3,4-Dimethyl-indole & 3,6-Dimethyl-indole | 82.0 | 45.0 | 36.9 |
| 9 | N—Methyl-m-toluidine | A | 275 | 1,3,4-Trimethyl-indole & 1,3,6-Trimethyl-indole | 55.8 | 47.3 | 26.4 |
| 10 | N—Ethyl-m-toluidine | A | 300 | 1-Ethyl-3,4-dimethylindole & 1-Ethyl-3,6-dimethylindole | 50.6 | 30.8 | 15.6 |
| 11 | p-Toluidine | B | 300 | 3,5-Dimethyl-indole | 76.2 | 31.5 | 24.0 |
| 12 | N—Methyl-p-toluidine | A | 300 | 1,3,5-Trimethyl-indole | | 72.8 | 49.1 |
| | | | | 1,2,5-Trimethyl-indole | 67.5 | 20.6 | 13.9 |
| 13 | N—Ethyl-p-toluidine | A | 300 | 1-Ethyl-3,5-dimethylindole | | 73.7 | 37.0 |
| | | | | 1-Ethyl-2,5-dimethylindole | 50.2 | 19.3 | 9.7 |

TABLE 3-continued

| No. | Anilines | Reaction conditions | Reaction temperature (°C.) | Main indoles produced | Conversion of anilines (%) | Selectivity to main indoles produced (%) | Yield of main indoles produced (%) |
|---|---|---|---|---|---|---|---|
| 14 | N—Methyl-p-anisidine | B | 300 | 1,3-dimethyl-5-methoxyindole | 67.4 | 44.4 | 29.9 |

EXAMPLE 4

The reaction was carried out in the same manner as described in Example 1 except that propylene oxide was used instead of ethylene glycol. The results are shown in the following Table 4.

| Reaction conditions | |
|---|---|
| Contact time (W/F): 49.6 g-cat · hr/mole | |
| Initial partial pressure (atm): | |
| Anilines vapor | 0.0205 |
| Propylene oxide vapor | 0.0409 |
| Water vapor | 0.778 |
| Nitrogen gas | 0.161 |

TABLE 4

| No. | Anilines | Reaction temperature (°C.) | Main indoles produced | Conversion of anilines (%) | Selectivity to main indoles produced (%) | Yield of main indoles produced (%) |
|---|---|---|---|---|---|---|
| 1 | Aniline | 350 | 3-Methyl-indole | 55.7 | 21.5 | 12.0 |
| 2 | N—Methyl-aniline | 300 | 1,3-Di-methyl-indole | | 38.5 | 19.6 |
|   |   |   | 1,2-Di-methyl-indole | 50.9 | 9.4 | 4.8 |
| 3 | N—Ethyl-aniline | 300 | 1-Ethyl-3-methyl-indole | | 36.7 | 17.5 |
|   |   |   | 1-Ethyl-2-methyl-indole | 47.7 | 8.0 | 3.8 |

EXAMPLE 5

The reaction was carried out in the same manner as described in Example 1 except that ethylene glycol monomethyl ether was used instead of ethylene glycol. The results are shown in the following Table 5.

| Reaction conditions | |
|---|---|
| Contact time (W/F) | 49.6 g-cat · hr/mole |
| Initial partial pressure (atm) | |
| Anilines vapor | 0.0205 |
| Ethylene glycol monomethyl ether vapor | 0.0409 |
| Water vapor | 0.778 |
| Nitrogen gas | 0.161 |

TABLE 5

| No. | Anilines | Reaction temperature (°C.) | Main indoles produced | Conversion of anilines (%) | Selectivity to main indoles produced (%) | Yield of main indoles produced (%) |
|---|---|---|---|---|---|---|
| 1 | N—Methyl-aniline | 325 | 1-Methyl-indole | 80.7 | 34.0 | 27.4 |
| 2 | N—Ethyl-aniline | 325 | 1-Ethyl-indole | 69.5 | 34.8 | 24.2 |

EXAMPLE 6

The reaction was carried out in the same manner as described in Example 1 except that ethylene glycol mono-n-butyl ether was used instead of ethylene glycol. The results are shown in the following Table 6.

| Reaction conditions | |
|---|---|
| Contact time (W/F) | 49.6 g-cat · hr/mole |
| Initial partial pressure (atm) | |
| Anilines vapor | 0.0205 |
| Ethylene glycol mono-n-buthyl ether vapor | 0.0409 |
| Water vapor | 0.778 |
| Nitrogen gas | 0.161 |

TABLE 6

| No. | Anilines | Reaction temperature (°C.) | Main indoles produced | Conversion of anilines (%) | Selectivity to main indoles produced (%) | Yield of main indoles produced (%) |
|---|---|---|---|---|---|---|
| 1 | N—Methyl-aniline | 325 | 1-Methyl-indole | 52.1 | 46.9 | 24.5 |
| 2 | N—Ethyl-aniline | 325 | 1-Ethyl-indole | 58.6 | 33.1 | 19.4 |

EXAMPLE 7

The reaction was carried out in the same manner as described in Example 1 except that 1,2-buthylene glycol was used instead of ethylene glycol. The results are shown in the following Table 7.

| Reaction conditions | |
|---|---|
| Contact time (W/F) | 49.6 g-cat · hr/mole |
| Initial partial pressure (atm) | |
| Anilines vapor | 0.0205 |
| 1,2-Buthylene glycol vapor | 0.0307 |
| Water vapor | 0.788 |
| Nitrogen gas | 0.161 |

EXAMPLE 8

30 g of a catalyst shown in Table 8 were packed into a tubular quartz-reactor (22 mm in diameter, 300 mm in length), and then heated by a tubular electric furnace. A

TABLE 7

| No. | Anilines | Reaction temperature (°C.) | Main indoles produced | Conversion of anilines (%) | Selectivity to main indoles produced (%) | Yield of main indoles produced (%) |
|---|---|---|---|---|---|---|
| 1 | N—Ethyl-aniline | 300 | 1,3-diethyl-indole | 36.1 | 53.7 | 19.4 | mixed gas of aniline vapor, ethylene glycol vapor, water vapor and nitrogen gas was introduced into the reactor under the following conditions.

| Reaction conditions | |
|---|---|
| Contact time (W/F) | 74.4 g-cat · hr/mole |
| Initial partial pressure (atm) | |
| Aniline vapor | 0.0205 |
| Ethylene glycol vapor | 0.0819 |
| Water vapor | 0.737 |
| Nitrogen gas | 0.161 |

The effluent gas was cooled by a condensor and collected as a condensed solution. The condensed solution was analyzed by gas chromatography about 3 hours after the reaction was started. The results are shown in the following Table 8.

The chemical compositions (% by weight) of "Neobead P, C or D" (manufactured by Mizusawa Chenmical Industry Co., Ltd.) used as the catalyst are as follows:

"Neobead P"; $Al_2O_3:SiO_2:Na_2O = 88:9:3$
"Neobead C"; $Al_2O_3 = 100$
"Neobead D"; $Al_2O_3:SiO_2 = 90:10$

TABLE 8

| No. | Catalysts | Reaction temperature (°C.) | Conversion of aniline (%) | Selectivity to indole (%) | Yield of indole (%) |
|---|---|---|---|---|---|
| 1 | Neobead P | 300 | 82.3 | 15.4 | 12.7 |
|   |           | 350 | 71.0 | 18.3 | 13.0 |
| 2 | $Fe_2O_3$ (10%)-Neobead P | 300 | 91.0 | 14.9 | 13.6 |
|   |           | 350 | 76.1 | 16.0 | 12.2 |
| 3 | $Fe_2O_3$ (10%)-Neobead C | 300 | 80.9 | 10.9 | 8.8 |
|   |           | 350 | 78.8 | 17.5 | 13.8 |
| 4 | $Fe_2O_3$ (10%)-Neobead D | 300 | 96.9 | 14.3 | 13.9 |
|   |           | 350 | 75.5 | 16.4 | 12.4 |
| 5 | ZnO (10%)-Neobead C | 300 | 83.6 | 11.1 | 9.3 |
|   |           | 350 | 87.5 | 12.0 | 10.5 |
| 6 | $Cr_2O_3$ (10%)-Neobead C | 300 | 81.5 | 11.9 | 9.7 |
|   |           | 350 | 74.5 | 14.1 | 10.5 |
| 7 | NiO (10%)-Neobead C | 350 | 74.2 | 21.1 | 15.7 |
|   |           | 400 | 41.4 | 23.7 | 9.8 |

EXAMPLE 9

The reaction of N-ethylaniline with ethylene glycol was carried out over a catalyst shown in Table 9 in the same manner as described in Example 1, whereby 1-ethylindole was obtained as a main product. The results are shown in the following Table 9.

| Reaction conditions A | |
|---|---|
| Contact time (W/F) | 49.6 g-cat · hr/mole |
| Initial partial pressure (atm) | |
| N—Ethylaniline vapor | 0.0205 |
| Ethylene glycol vapor | 0.0409 |
| Water vapor | 0.778 |
| Nitrogen gas | 0.161 |
| Reaction conditions B | |
| Contact time (W/F) | 24.8 g-cat · hr/mole |
| Initial partial pressure (atm) | |
| N—Ethylaniline vapor | 0.0205 |
| Ethylene glycol vapor | 0.0409 |
| Water vapor | 0.778 |
| Nitrogen gas | 0.161 |

TABLE 9

| No. | Catalysts | Reaction conditions | Reaction temperature (°C.) | Conversion of N—ethyl-aniline (%) | Selectivity to 1-ethyl-indole (%) | Yield of 1-ethyl-indole (%) |
| --- | --- | --- | --- | --- | --- | --- |
| 1 | Neobead P | A | 300 | 58.7 | 71.9 | 42.2 |
| 2 | Neobead P | B | 350 | 53.5 | 52.1 | 27.9 |
| 3 | NiO (10%)-Neobead P | B | 350 | 38.5 | 56.1 | 21.6 |
| 4 | Neobead D | A | 250 | 56.9 | 22.3 | 12.7 |
| 5 | Neobead C | A | 250 | 46.5 | 19.8 | 9.2 |
| 6 | $K_2O$ (1%)-Neobead C | A | 300 | 75.8 | 35.2 | 26.7 |
| 7 | $K_2O$ (3%)-Neobead C | A | 300 | 56.0 | 45.5 | 25.5 |
| 8 | $K_2O$ (5%)-Neobead C | A | 300 | 37.6 | 73.9 | 27.8 |
| 9 | $K_2O$ (7%)-Neobead C | A | 350 | 50.6 | 62.8 | 31.8 |
| 10 | $K_2O$ (10%)-Neobead C | A | 350 | 33.8 | 47.6 | 16.1 |

EXAMPLE 10

20 g of a catalyst shown in Table 10 were packed into a tubular quartz-reactor (22 mm in diameter, 300 mm in length), and then heated by a tubular electric furnace. A mixed gas of aniline vapor, ethylene oxide vapor, water vapor and nitrogen gas was introduced into the reactor under the following conditions.

| Reaction conditions | |
| --- | --- |
| Contact time (W/F) | 49.6 g-cat · hr/mole |
| Initial partial pressure (atm) | |
| Aniline vapor | 0.0204 |
| Ethylene oxide vapor | 0.0224 |
| Water vapor | 0.796 |
| Nitrogen gas | 0.161 |

The effuent gas was cooled by a condensor and collected as a condensed solution. The condensed solution was analyzed by gas chromatography about 3 hours after the reaction was started. The results are shown in the following Table 10.

The chemical compositions (% by weight) of "Silica" (manufactured by Katayama Chemical Industry Co., Ltd.); $SiO_2 = 100$

TABLE 10

| No. | Catalysts | Reaction temperature (°C.) | Conversion of aniline (%) | Selectivity to indole (%) | Yield of indole (%) |
| --- | --- | --- | --- | --- | --- |
| 1 | Neobead P | 350 | 42.1 | 32.1 | 13.5 |
| 2 | Silica | 400 | 62.6 | 15.8 | 9.9 |

EXAMPLE 11

N-Ethylaniline and ethylene glycol were reacted at a molar ratio shown in Table 11 in the same manner as described in Example 1, whereby 1-ethylindole was obtained as a main product. The results are shown in the following Table 11.

| Reaction conditions | | |
| --- | --- | --- |
| Reaction temperature | | 300° C. |
| Contact time (W/F) | | 49.6 g-cat · hr/mole |
| Initial partial pressure (atm) | | |
| N—Ethyaniline vapor | | 0.0205 |
| Nitrogen gas | | 0.161 |
| Water vapor | (A) 0.808 | (B) 0.798 |
| | (C) 0.778 | (D) 0.757 |

TABLE 11

| No. | Molar ratio (Ethylene glycol / N—Ethylaniline) | Reaction conditions | Conversion of N—ethyl-aniline (%) | Selectivity to 1-ethyl-indole (%) | Yield of 1-ethyl-indole (%) |
| --- | --- | --- | --- | --- | --- |
| 1 | 0.5 | A | 39.5 | 71.0 | 28.0 |
| 2 | 1.0 | B | 59.9 | 67.9 | 40.7 |
| 3 | 2.0 | C | 58.7 | 71.9 | 42.2 |
| 4 | 3.0 | D | 53.3 | 83.5 | 44.5 |

EXAMPLE 12

N-Ethylaniline and ethylene glycol were reacted at a contact time shown in Table 12 in the same manner as described in Example 1, whereby 1-ethylindole was obtained as a main product. The results are shown in the following Table 12.

| Reaction conditions | |
| --- | --- |
| Reaction temperature | 300° C. |
| Initial partial pressure (atm) | |
| N—Ethylaniline vapor | 0.0205 |
| Ethylene glycol vapor | 0.0409 |
| Water vapor | 0.778 |
| Nitrogen gas | 0.161 |

TABLE 12

| No. | Contact time (W/F) (g-cat · hr/mole) | Conversion of N—ethyl-aniline (%) | Selectivity to 1-ethyl-indole (%) | Yield of 1-ethyl-indole (%) |
| --- | --- | --- | --- | --- |
| 1 | 12.4 | 15.9 | 85.5 | 13.6 |
| 2 | 24.8 | 37.4 | 61.0 | 22.8 |
| 3 | 37.2 | 39.5 | 69.4 | 27.4 |
| 4 | 49.6 | 58.7 | 71.9 | 42.2 |

TABLE 12-continued

| No. | Contact time (W/F) (g-cat · hr/mole) | Conversion of N—ethyl-aniline (%) | Selectivity to 1-ethyl-indole (%) | Yield of 1-ethyl-indole (%) |
|---|---|---|---|---|
| 5 | 74.3 | 78.7 | 61.6 | 48.5 |

EXAMPLE 13

N-Ethylaniline and ethylene glycol were reacted in the same manner as described in Example 1 by adjusting the initial partial pressure as shown in Table 13, whereby 1-ethylindole was obtained as a main product. The results are shown in the following Table 13.

| Reaction conditions | |
|---|---|
| Reaction temperature | 300° C. |
| Contact time (W/F) | 49.6 g-cat · hr/mole |

Molar ratio $\left(\dfrac{\text{Ethylene glycol}}{\text{N—Ethylaniline}}\right)$ 2

Initial partial pressure (atm)
| | | |
|---|---|---|
| Nitrogen gas | | 0.161 |
| Water vapor | (A) 0.825 | (B) 0.808 |
| | (C) 0.778 | (D) 0.716 |
| | (E) 0.532 | |

TABLE 13

| No. | Initial partial pressure of N—ethylaniline (atm) | Reaction conditions | Conversion of N—ethyl-aniline (%) | Selectivity to 1-ethyl-indole (%) | Yield of 1-ethyl-indole (%) |
|---|---|---|---|---|---|
| 1 | 0.00462 | A | 70.3 | 45.9 | 32.3 |
| 2 | 0.0102 | B | 59.1 | 62.8 | 37.1 |
| 3 | 0.0205 | C | 58.7 | 71.9 | 42.2 |
| 4 | 0.0409 | D | 42.0 | 68.3 | 28.7 |
| 5 | 0.102 | E | 14.8 | 56.1 | 8.3 |

EXAMPLE 14

N-Ethylaniline and ethylene glycol were reacted in the same manner as described in Example 1, by using benzene vapor as the diluent gas or without using said vapor, whereby 1-ethylindole was obtained as a main product. The results are shown in the following Table 14.

| Reaction conditions | |
|---|---|
| Contact time (W/F) | 49.6 g-cat · hr/mole |
| Initial partial pressure (atm) | |
| N—Ethylaniline vapor | 0.0205 |
| Ethylene glycol vapor | 0.0409 |
| Nitrogen gas | 0.161 |

| Reaction conditions | (A) | (B) |
|---|---|---|
| Water vapor | 0.778 | 0.659 |
| Benzene vapor | — | 0.119 |

TABLE 14

| No. | Benzene vapor | Reaction conditions | Reaction temperature (°C.) | Conversion of N—ethylaniline (%) | Selectivity to 1-ethylindole (%) | Yield of 1-ethylindole (%) |
|---|---|---|---|---|---|---|
| 1 | Nil | A | 300 | 58.7 | 71.9 | 42.2 |
|   |     |   | 350 | 57.9 | 6.6 | 3.8 |
| 2 | Yes | B | 300 | 37.3 | 87.1 | 32.5 |
|   |     |   | 350 | 58.9 | 48.6 | 28.6 |

EXAMPLE 15

N-Methylaniline and ethylene glycol were reacted at a contact time shown in Table 15 in the same manner as described in Example 1, whereby 1-methylindole was obtained as a main product. The results are shown in the following Table 15.

| Reaction conditions | |
|---|---|
| Reaction temperature | 300° C. |
| Initial partial pressure (atm): | |
| N—Methylaniline vapor | 0.0205 |
| Ethylene glycol vapor | 0.0409 |
| Water vapor | 0.778 |
| Nitrogen gas | 0.161 |

TABLE 15

| No. | Contact time (W/F) (g-cat · hr/mole) | Conversion of N—methyl-aniline (%) | Selectivity to 1-methyl-indole (%) | Yield of 1-methyl-indole (%) |
|---|---|---|---|---|
| 1 | 12.4 | 24.3 | 25.1 | 6.1 |
| 2 | 24.8 | 35.6 | 51.4 | 18.3 |
| 3 | 37.2 | 48.6 | 66.0 | 32.1 |
| 4 | 49.6 | 56.7 | 63.5 | 36.0 |
| 5 | 74.3 | 74.9 | 57.8 | 43.3 |
| 6 | 93.8 | 70.5 | 82.0 | 57.8 |

EXAMPLE 16

N-Benzylaniline and ethylene glycol were reacted at a molar ratio shown in Table 16 in the same manner as described in Example 1, whereby 1-benzylindole was obtained as a main product. The results are shown in the following Table 16.

| Reaction condition | |
|---|---|
| Reaction temperature | 300° C. |
| Contact time (W/F) | 49.6 g-cat · hr/mole |
| Initial partial pressure (atm): | |
| N—Benzylaniline vapor | 0.0205 |
| Nitrogen gas | 0.161 |

-continued

| Reaction condition | |
|---|---|
| Benzene vapor | 0.119 |
| Water vapor | (A) 0.689 (B) 0.679 |
| | (C) 0.659 (D) 0.638 |
| | (E) 0.618 |

TABLE 16

| No. | Molar ratio (Ethylene glycol / N—Benzylaniline) | Reaction conditions | Conversion of N—benzyl-aniline (%) | Selectivity to 1-benzyl-indole (%) | Yield of 1-benzyl-indole (%) |
|---|---|---|---|---|---|
| 1 | 0.5 | A | 38.7 | 39.5 | 15.3 |
| 2 | 1.0 | B | 45.0 | 61.9 | 27.9 |
| 3 | 2.0 | C | 82.8 | 49.4 | 40.9 |
| 4 | 3.0 | D | 55.5 | 80.7 | 44.8 |
| 5 | 4.0 | E | 54.4 | 92.5 | 50.5 |

EXAMPLE 17

Aniline and propylene glycol were reacted at a molar ratio shown in Table 17 in the same manner as described in Example 1, whereby 3-methylindole was obtained as a main product. The results are shown in the following Table 17.

EXAMPLE 18

N-Methylaniline and propylene glycol were reacted at a molar ratio shown in Table 18 in the same manner as described in Example 1, whereby 1,3-dimethylindole and 1,2-dimethylindole were obtained as main products. The results are shown in the following Table 18.

| Reaction conditions | |
|---|---|
| Reaction temperature | 300° C. |
| Contact time (W/F) | 49.6 g-cat · hr/mole |
| Initial partial pressure (atm): | |
| N—Methylaniline vapor | 0.0205 |
| Nitrogen gas | 0.161 |
| Water vapor | (A) 0.808 (B) 0.798 |
| | (C) 0.778 (D) 0.757 |
| | (E) 0.716 |

TABLE 18

| No. | Molar ratio (Propylene glycol / N—Methylaniline) | Reaction conditions | Main indoles produced | Conversion of N—methyl-anilines (%) | Selectivity to main indoles produced (%) | Yield of main indoles produced (%) |
|---|---|---|---|---|---|---|
| 1 | 0.5 | A | 1,3-dimethylindole | 35.3 | 44.2 | 15.6 |
| | | | 1,2-dimethylindole | | 18.4 | 6.5 |
| 2 | 1.0 | B | 1,3-dimethylindole | 45.5 | 48.8 | 22.2 |
| | | | 1,2-dimethylindole | | 19.3 | 8.8 |
| 3 | 2.0 | C | 1,3-dimethylindole | 50.3 | 46.1 | 23.2 |
| | | | 1,2-dimethylindole | | 14.5 | 7.3 |
| 4 | 3.0 | D | 1,3-dimethylindole | 43.4 | 51.2 | 22.2 |
| | | | 1,2-dimethylindole | | 24.9 | 10.8 |
| 5 | 5.0 | E | 1,3-dimethylindole | 43.6 | 55.0 | 24.0 |
| | | | 1,2-dimethylindole | | 22.2 | 9.7 |

EXAMPLE 19

N-Methylaniline and propylene glycol were reacted at a contact time shown in Table 19 in the same manner as described in Example 1, whereby 1,3-dimethylindole and 1,2-dimethylindole were obtained as main products. The results are shown in the following Table 19.

| Reaction conditions | |
|---|---|
| Reaction temperature | 300° C. |
| Contact time (W/F) | 49.6 g-cat · hr/mole |
| Initial partial pressure (atm): | |
| Aniline vapor | 0.0205 |
| Nitrogen gas | 0.161 |
| Water vapor | (A) 0.808 (B) 0.798 |
| | (C) 0.778 (D) 0.757 |
| | (E) 0.737 |

| Reaction conditions | |
|---|---|
| Reaction temperature: | 300° C. |
| Initial partial pressure (atm): | |
| N—Methylaniline vapor | 0.0205 |
| Propylene glycol vapor | 0.0409 |
| Water vapor | 0.778 |
| Nitrogen gas | 0.161 |

TABLE 17

| No. | Molar ratio (Propylene glycol / Aniline) | Reaction conditions | Conversion of aniline (%) | Selectivity to 3-methyl-indole (%) | Yield of 3-methyl-indole (%) |
|---|---|---|---|---|---|
| 1 | 0.5 | A | 21.1 | 39.3 | 8.3 |
| 2 | 1.0 | B | 30.6 | 39.2 | 12.2 |
| 3 | 2.0 | C | 63.4 | 31.9 | 20.2 |
| 4 | 3.0 | D | 74.7 | 27.8 | 20.8 |
| 5 | 4.0 | E | 78.9 | 24.6 | 19.4 |

TABLE 19

| No. | Contact time (W/F) (g-cat · hr/mole) | Main indoles produced | Conversion of N—methyl-aniline (%) | Selectivity to main indoles produced (%) | Yield of main indoles produced (%) |
|---|---|---|---|---|---|
| 1 | 12.4 | 1,3-dimethylindole | 18.0 | 26.7 | 4.8 |
|   |      | 1,2-dimethylindole |      | 15.6 | 2.8 |
| 2 | 24.8 | 1,3-dimethylindole | 31.9 | 22.9 | 7.3 |
|   |      | 1,2-dimethylindole |      | 9.1  | 2.9 |
| 3 | 37.2 | 1,3-dimethylindole | 47.9 | 38.2 | 18.3 |
|   |      | 1,2-dimethylindole |      | 15.4 | 7.4 |
| 4 | 46.9 | 1,3-dimethylindole | 50.3 | 46.1 | 23.2 |
|   |      | 1,2-dimethylindole |      | 14.5 | 7.3 |
| 5 | 74.3 | 1,3-dimethylindole | 58.0 | 49.8 | 28.9 |
|   |      | 1,2-dimethylindole |      | 14.3 | 8.3 |
| 6 | 93.8 | 1,3-dimethylindole | 63.0 | 47.5 | 29.9 |
|   |      | 1,2-dimethylindole |      | 9.7  | 6.1 |

EXAMPLE 20

N-Methylaniline and propylene oxide were reacted at a molar ratio shown in Table 20 in the same manner as described in Example 1, whereby 1,3-dimethylindole and 1,2-dimethylindole were obtained as main products. The results are shown in the following Table 20.

| Reaction conditions | |
|---|---|
| Reaction temperature | 300° C. |
| Contact time (W/F) | 49.6 g-cat · hr/mole |
| Initial partial pressure (atm): | |
| N—Methylaniline vapor | 0.0205 |
| Nitrogen gas | 0.161 |
| Water vapor | (A) 0.808 (B) 0.798 |
|  | (C) 0.778 (D) 0.757 |
|  | (E) 0.716 |

TABLE 20

| No. | Molar ratio (Propylene oxide / N—Methylaniline) | Reaction conditions | Main indoles produced | Conversion of N—methyl-anilines (%) | Selectivity to main indoles produced (%) | Yield of main indoles produced (%) |
|---|---|---|---|---|---|---|
| 1 | 0.5 | A | 1,3-dimethylindole | 31.2 | 52.6 | 16.4 |
|   |     |   | 1,2-dimethylindole |      | 14.4 | 4.5 |
| 2 | 1.0 | B | 1,3-dimethylindole | 46.7 | 44.8 | 20.9 |
|   |     |   | 1,2-dimethylindole |      | 12.0 | 5.6 |
| 3 | 2.0 | C | 1,3-dimethylindole | 50.9 | 38.5 | 19.6 |
|   |     |   | 1,2-dimethylindole |      | 9.4  | 4.8 |
| 4 | 3.0 | D | 1,3-dimethylindole | 46.4 | 48.1 | 22.3 |
|   |     |   | 1,2-dimethylindole |      | 13.4 | 6.2 |
| 5 | 5.0 | E | 1,3-dimethylindole | 49.3 | 40.8 | 20.1 |
|   |     |   | 1,2-dimethylindole |      | 11.0 | 5.4 |

We claim:

1. A process for preparing an indole which consists essentially of reacting in the vapor phase an aniline of the formula

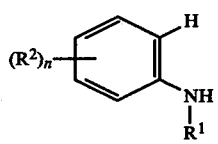
(I)

wherein $R^1$ is hydrogen, alkyl, aryl or aralkyl, $R^2$ is alkyl or alkoxy, and n is an integer of 0 to 4, with a glycol of the formula:

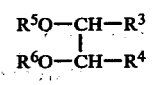
(II)
$$R^5O-CH-R^3$$
$$R^6O-CH-R^4$$

wherein $R^3$ and $R^4$ are the same or different and stand for hydrogen or alkyl, and $R^5$ and $R^6$ are the same or different and stand for hydrogen or alkyl, or an oxide of the formula:

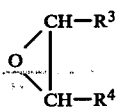
(II')

wherein $R^3$ and $R^4$ are the same as defined above, at 250° to 400° C. in the presence of a solid acid catalyst selected from the group consisting of silica, alumina, and silica-alumina to give an indole of the formula:

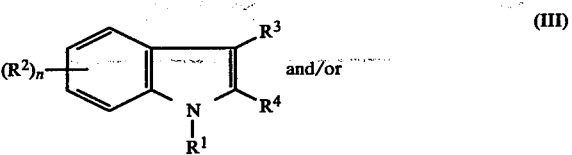
(III)

and/or

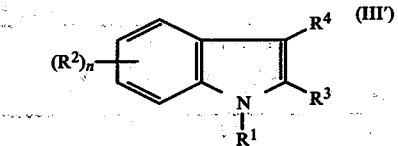
(III')

wherein $R^1$, $R^2$, $R^3$, $R^4$ and n are the same as defined above.

2. The process according to claim 1, wherein the solid acid catalyst further contains a metal oxide selected from the group consisting of an alkali metal oxide, zinc oxide, chromium oxide, iron oxide and nickel oxide.

3. The process according to claim 2, wherein the solid acid catalyst is silica-alumina catalyst containing a metal oxide selected from the group consisting of an alkali metal oxide, zinc oxide, chromium oxide, iron oxide and nickel oxide.

4. The process according to claim 2, wherein the solid acid catalyst is silica-alumina catalyst containing an alkali metal oxide.

5. The process according to claim 4, wherein the solid acid catalyst is silica-alumina catalyst containing sodium oxide.

6. The process according to claim 1 or 2, wherein the vapor phase reaction is carried out by contacting a gaseous mixture of the aniline (I), the glycol (II) or the oxide (II'), and an inert diluent with the solid acid catalyst.

7. The process according to claim 1 or 2, wherein the vapor phase reaction is carried out by contacting a gaseous mixture of the aniline (I), 0.5 to 10 moles of the glycol (II) or the oxide (II') per mole of said aniline (I), and an inert diluent with the solid acid catalyst at a contact time of 10 to 1,000 g-cat.hr/mole.

8. The process according to claim 1 or 2, wherein the vapor phase reaction is carried out by contacting a gaseous mixture of the aniline (I), 0.5 to 10 moles of the glycol (II) or the oxide (II') per mole of said aniline (I), and an inert diluent with the solid acid catalyst at 275° to 350° C. at a contact time of 20 to 200 g-cat.hr/mole under atmospheric pressure.

* * * * *